(12) United States Patent
Park et al.

(10) Patent No.: US 9,084,580 B2
(45) Date of Patent: Jul. 21, 2015

(54) APPARATUS AND METHOD FOR GENERATING ULTRASONIC IMAGE

(75) Inventors: Sung Chan Park, Suwon-si (KR); Jung Ho Kim, Yongin-si (KR); Kyu Hong Kim, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 336 days.

(21) Appl. No.: 13/592,659

(22) Filed: Aug. 23, 2012

(65) Prior Publication Data

US 2013/0231563 A1    Sep. 5, 2013

(30) Foreign Application Priority Data

Mar. 2, 2012    (KR) .................. 10-2012-0021976

(51) Int. Cl.
| | | |
|---|---|---|
| *A61B 8/14* | (2006.01) | |
| *G06F 19/00* | (2011.01) | |
| *A61B 8/08* | (2006.01) | |
| *G01S 15/89* | (2006.01) | |
| *G01S 7/52* | (2006.01) | |

(52) U.S. Cl.
CPC ........... *A61B 8/5207* (2013.01); *G01S 7/52046* (2013.01); *G01S 7/52047* (2013.01); *G01S 15/8977* (2013.01); *A61B 8/5269* (2013.01)

(58) Field of Classification Search
CPC ............ G01S 7/52047; G01S 7/52046; G01S 15/8977
USPC ................... 73/606, 625, 626; 600/443, 447
See application file for complete search history.

(56) References Cited

U.S. PATENT DOCUMENTS

| | | | | |
|---|---|---|---|---|
| 6,443,895 | B1 * | 9/2002 | Adam et al. ................... | 600/443 |
| 6,689,063 | B1 * | 2/2004 | Jensen et al. .................. | 600/443 |
| 7,025,724 | B2 * | 4/2006 | Adam et al. ................... | 600/437 |
| 8,306,293 | B2 * | 11/2012 | Walker et al. ................ | 382/128 |
| 8,756,033 | B2 * | 6/2014 | Ishikawa et al. .............. | 702/150 |
| 2002/0049379 | A1 | 4/2002 | Adam et al. | |
| 2004/0054281 | A1 | 3/2004 | Adam et al. | |
| 2007/0167802 | A1 * | 7/2007 | Rigby et al. .................. | 600/459 |

FOREIGN PATENT DOCUMENTS

| | | |
|---|---|---|
| KR | 10-2007-0119879 A | 12/2007 |
| KR | 10-2010-0010481 A | 2/2010 |

* cited by examiner

*Primary Examiner* — J M Saint Surin
(74) *Attorney, Agent, or Firm* — NSIP Law

(57) ABSTRACT

An apparatus and method for generating an ultrasonic image are provided. The apparatus includes a transceiver configured to transmit an ultrasonic signal to an object, and receive an echo signal. The apparatus further includes a beam former configured to perform beamforming on the received echo signal to generate image data. The apparatus further includes a point spread function (PSF) estimator configured to update a PSF of the ultrasonic signal at each multiscale level to update the image data.

20 Claims, 4 Drawing Sheets

100

APPARATUS AND METHOD FOR GENERATING ULTRASONIC IMAGE

CROSS-REFERENCE TO RELATED APPLICATION(S)

This application claims the benefit under 35 U.S.C. §119 (a) of Korean Patent Application No. 10-2012-0021976, filed on Mar. 2, 2012, in the Korean Intellectual Property Office, the entire disclosure of which is incorporated herein by reference for all purposes.

BACKGROUND

1. Field

The following description relates to an apparatus and method for generating an ultrasonic image.

2. Description of Related Art

A market for a medical ultrasonic imaging device providing anatomical and functional information about internal parts of a human body in real-time and in a non-invasive and harmless manner, is growing steadily. A role of an apparatus configured to generate an ultrasonic image in various industrial environments in addition to the medical field, is also increasing.

To generate an ultrasonic image of an object, the ultrasonic imaging apparatus may transmit an ultrasonic wave to the object using a transducer configured to transmit and receive an ultrasonic wave, receive information reflected from the object, and perform a beamforming process, also referred to as a focusing process. However, technical properties of the ultrasonic wave may cause technical problems, such as, for example, a significant amount of noise, a quality of an ultrasonic image greatly affected by a scatter reflection due to a tissue in the object, and/or other technical problems known to one of ordinary skill in the art.

Accordingly, to increase a resolution of the ultrasonic image, a correlation between a pattern of the ultrasonic wave and a value of the scatter reflection has been modeled and used in an image rendering process. In such a process, a process of estimating a point spread function (PSF) of the pattern has also been used. Conventional processes of estimating the PSF include estimating the PSF in a frequency domain, estimating the PSF in a spatial domain, and/or other processes known to one of ordinary skill in the art. However, the conventional processes provide a limited improvement in a resolution of an ultrasonic image due to an error in phase estimation and/or other limitations known to one of ordinary skill in the art.

SUMMARY

In one general aspect, there is provided an apparatus configured to generate an ultrasonic image, the apparatus including a transceiver configured to transmit an ultrasonic signal to an object, and receive an echo signal. The apparatus further includes a beam former configured to perform beamforming on the received echo signal to generate image data. The apparatus further includes a point spread function (PSF) estimator configured to update a PSF of the ultrasonic signal at each multiscale level to update the image data.

The apparatus may further include a renderer configured to generate the ultrasonic image including an increased resolution based on deconvolution of the updated PSF from the image data.

The PSF estimator may be further configured to apply different bases to an axial direction and a lateral direction of the PSF to update the PSF.

The PSF estimator may be further configured to select, at a high multiscale level, a basis to be applied to an axial direction of the PSF that includes a relatively narrow width, to update the PSF. The PSF estimator may be further configured to select, at a low multiscale level, a basis to be applied to the axial direction of the PSF that includes a relatively wide width, to update the PSF.

The PSF estimator may be further configured to estimate, at a high multiscale level, a one-dimensional PSF based on an axial direction of the PSF. The PSF estimator may be further configured to estimate, at a low multiscale level, a multi-dimensional PSF based on the axial direction and other directions of the PSF. The PSF estimator may be further configured to update the PSF based on the one-dimensional PSF and the multi-dimensional PSF.

The PSF estimator may be further configured to set a value determined through a simulation as an initial value of the PSF.

The PSF estimator may be further configured to set a value measured in a real environment as an initial value of the PSF.

In another general aspect, there is provided an apparatus configured to generate an ultrasonic image, the apparatus including a transceiver configured to transmit an ultrasonic signal to an object, and receive an echo signal. The apparatus further includes a beam former configured to perform a delay-and-sum operation on the received echo signal to generate image data. The apparatus further includes a point spread function (PSF) estimator configured to apply different bases to an axial direction and a lateral direction of a PSF of the ultrasonic signal to update the PSF and the image data.

The apparatus may further include a renderer configured to generate the ultrasonic image including a resolution corresponding to a required display environment based on deconvolution of the updated PSF from the image data.

In still another general aspect, there is provided a method of generating an ultrasonic image, the method including transmitting an ultrasonic signal to an object. The method further includes receiving an echo signal. The method further includes performing beamforming on the received echo signal to generate image data. The method further includes updating a point spread function (PSF) of the ultrasonic signal at each multiscale level to update the image data.

The method may further include generating the ultrasonic image including an increased resolution based on deconvolution of the updated PSF from the image data.

The updating may include applying different bases to an axial direction and a lateral direction of the PSF to update the PSF.

The updating may include selecting, at a high multiscale level, a basis to be applied to an axial direction of the PSF that includes a relatively narrow width, to update the PSF. The updating may further include selecting, at a low multiscale level, a basis to be applied to the axial direction of the PSF that includes a relatively wide width, to update the PSF.

A non-transitory computer-readable storage medium may store a program to generate an ultrasonic image, including instructions to cause a computer to perform the method.

In yet another general aspect, there is provided a method of generating an ultrasonic image, the method including transmitting an ultrasonic signal to an object. The method further includes receiving an echo signal. The method further includes performing a delay-and-sum operation on the received echo signal to generate image data. The method further includes applying different bases to an axial direction and a lateral direction of a point spread function (PSF) of the ultrasonic signal to update the PSF and the image data.

The applying may include updating the PSF at each multiscale level.

The applying may include selecting, at a high multiscale level, a basis to be applied to the axial direction of the PSF that includes a relatively narrow width, to update the PSF. The updating may further include selecting, at a low multiscale level, a basis to be applied to the axial direction of the PSF that includes a relatively wide width, to update the PSF.

A non-transitory computer-readable storage medium may store a program to generate an ultrasonic image, including instructions to cause a computer to perform the method.

Other features and aspects will be apparent from the following detailed description, the drawings, and the claims.

Figure 1:
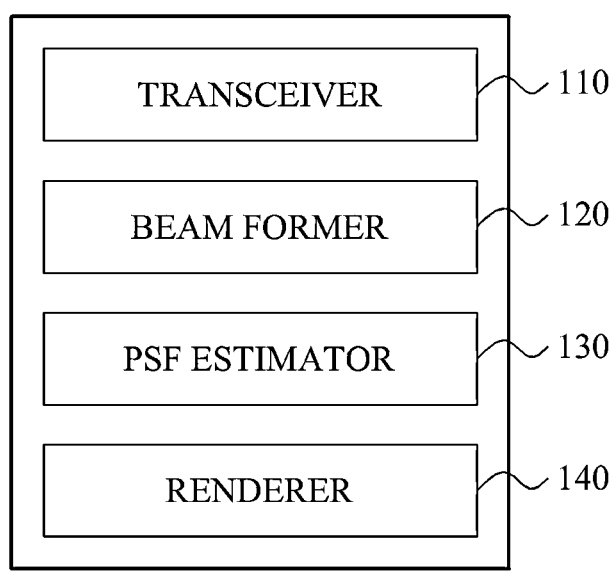
FIG. 1 is a block diagram illustrating an example of an apparatus configured to generate an ultrasonic image.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, description of well-known functions and constructions may be omitted for increased clarity and conciseness.

FIG. 1 illustrates an example of an apparatus 100 configured to generate an ultrasonic image. To generate the ultrasonic image of an object, raw file (RF) image data is generated after beamforming. The RF image data may be generated based on an interaction model between a pattern of an ultrasonic wave transmitted by the apparatus 100 to the object, to generate the RF image data, and a scatter reflection due to a tissue in the object, as given in the example of Equation 1.

$$g = f * h + w, \quad (1)$$

where g denotes the RF image data, f denotes the scatter reflection representing reflection properties of the object with respect to the ultrasonic wave, h denotes the pattern of the ultrasonic wave, and w denotes a noise.

That is, to generate the RF image data g, the noise w is added to a convolution of the scatter reflection f of the object and the pattern h of the ultrasonic wave.

In this example, a resolution of the ultrasonic image is changed based on the pattern h of the ultrasonic wave. If the pattern h is spread widely in a spatial sense, a resolution of the RF image data g is relatively low, even if the pattern h includes a broadband spatial frequency. Conversely, if the pattern h is concentrated narrowly in a spatial sense, the resolution of the RF image data g is relatively high.

In this example, when the pattern h of the ultrasonic wave is estimated, the scatter reflection f of the object may be estimated accurately based on deconvolution of the pattern h from the RF image data g. The foregoing method may be understood by a similar method of inputting an impulse into an electric circuit to determine a transfer function.

Accordingly, when the pattern h of the ultrasonic wave is estimated, a high resolution scatter reflection image of tissues of the object corresponding to the scatter reflection f of the object may be estimated, and an ultrasonic image including a high resolution may be rendered based on the scatter reflection image. In this example, the pattern h refers to as a point spread function (PSF).

The estimation of the pattern h of the ultrasonic wave, or the PSF, may be performed in a frequency domain or in a spatial domain. In a method of estimating the pattern h in the frequency domain, phase information is removed from the ultrasonic wave, a Wiener filter is applied to only magnitude information of the ultrasonic wave to estimate a magnitude of the PSF, and a phase of the PSF is estimated through phase unwrapping. However, a high probability of an error occurring in the estimation of the phase information exists. Accordingly, it may be difficult to obtain an image of a desired high resolution.

In a method of estimating the pattern h of the ultrasonic wave, or the PSF, in the spatial domain, a one-dimensional (1D) PSF is estimated in an axial direction using a maximum likelihood scheme. Then, 1D deconvolution is performed on the estimated 1D PSF using a Kalman filter or scheme. However, since only the 1D deconvolution is performed, an improvement in a resolution in only the axial direction may be expected, and an improvement in a resolution in a lateral direction or an elevation direction may not be readily expected.

Also, in another method of estimating the pattern h of the ultrasonic wave, or the PSF, a magnitude of the PSF is estimated in the frequency domain, a phase of the PSF is iteratively estimated using the maximum likelihood scheme, and deconvolution is performed on the estimated PSF using a conjugate gradient scheme in the spatial domain. However, this method may also include an issue in terms of quality degradation due to an error in the estimation of the phase, similar to the estimation of the phase in the frequency domain.

In the aforementioned methods, since a great number of hidden variables need to be estimated in two-dimensional (2D) PSF estimation when 2D deconvolution is performed, errors may occur, for example, in depending on an 1D PSF estimation, in utilizing a magnitude of a PSF estimated in a 2D frequency domain, in a phase estimation, and/or in other situations known to one of ordinary skill in the art. Accordingly, multiscale level-based deconvolution may be performed on an original PSF, as described herein. For example, high level deconvolution may be performed on an axial direction of the original PSF, and low level (e.g., 2D or three-dimensional (3D)) deconvolution may be performed on a lateral direction and an elevation direction of the deconvoluted PSF while progressively expanding to a low (i.e., lowest) level.

Referring to FIG. 1, the apparatus 100 includes a transceiver 110, a beam former 120, a PSF estimator 130, and a renderer 140. The transceiver 110 includes a transducer transmitting the ultrasonic wave or signal to the object, and receiving an echo signal reflected from the object.

When the transceiver 110 receives the echo signal, the beam former 120 performs beamforming (e.g., a delay-and-sum operation) on the received echo signal. The beamforming may be understood as a general process of generating the RF image data. The PSF estimator 130 progressively estimates a PSF at each multiscale level, and estimates a final PSF, or the pattern h of the ultrasonic wave, based on the estimated PSF at each multiscale level. That is, the PSF estimator 130 progressively updates an original PSF at each multiscale level to generate the final PSF.

When the PSF estimator 130 accurately estimates the final PSF, the renderer 140 estimates the scatter reflection f of the object based on deconvolution of the estimated final PSF from the generated RF image data. The renderer 140 further renders or generates the ultrasonic image corresponding to required display settings based on the estimated scatter reflection f of the object, and parameters of an accompanying filter calculation module.

Figure 2:
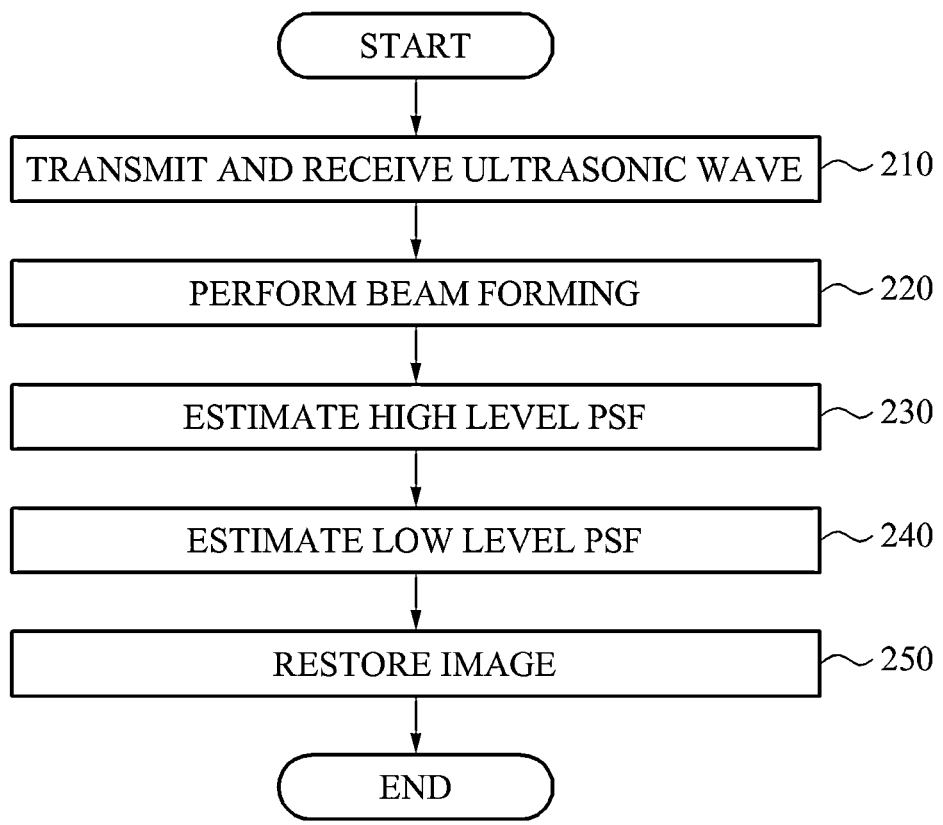
FIG. 2 is a flowchart illustrating an example of a method of generating an ultrasonic image.

FIG. 2 illustrates an example of a method of generating an ultrasonic image. The method of FIG. 2 may be performed by the apparatus 100 of FIG. 1 configured to generate the ultrasonic image of an object.

In operation 210, the transceiver 110 transmits an ultrasonic wave to the object, and receives an ultrasonic wave (e.g., an echo signal) reflected from the object. In operation 220, the beam former 120 performs beamforming (e.g., a focusing process and/or a delay-and-sum operation) on the received ultrasonic wave to generate RF image data.

In operations 230 and 240, the PSF estimator 130 estimates a PSF at each multiscale level. To estimate the PSF at each multiscale level, the PSF estimator 130 sequentially performs deconvolution on an original or previously-estimated PSF at each multiscale level. Operations 230 and 240 may be expanded to additional operations depending on various examples.

For example, in operation 230, the PSF estimator 130 estimates a PSF at a high level by performing deconvolution on an axial direction of the original PSF. In operation 240, the PSF estimator 130 estimates a PSF at a low or lower level by performing 2D or 3D deconvolution on the previously-estimated PSF at the high level. The PSF estimator 130 may estimate additional PSFs at lower levels progressively expanding to the low (i.e., lowest) level by performing 2D or 3D deconvolution on previously-estimated PSFs at higher levels. At the low level, the PSF estimator 130 estimates a final PSF based on the a previously-estimated PSF at a higher level. That is, the PSF estimator 130 progressively updates the original PSF at each multiscale level to generate the final PSF.

In this example, different bases may be applied to different directions, for example, the axial direction, a lateral direction, and/or other directions known to one of ordinary skill in the art, of the original or previously-estimated PSFs to perform deconvolution on the original and previously-estimated PSFs. A method of applying different bases will be further described in detail with reference to FIGS. 3 and 4. Through the deconvolution at the high and low levels, the original PSF is progressively updated to generate the final PSF accurately reflecting properties with respect to the lateral direction.

In operation 250, the renderer 140 restores an ultrasonic image in which a resolution of the RF image data is greatly improved. The restoration of the ultrasonic image includes accurately estimating the scatter reflection f of the object in Equation 1, corresponding to reflection properties of the object, based on deconvolution of the estimated final PSF from the generated RF image data. The restoration of the ultrasonic image further includes rendering the ultrasonic image based on the estimated scatter reflection f.

Figure 3:
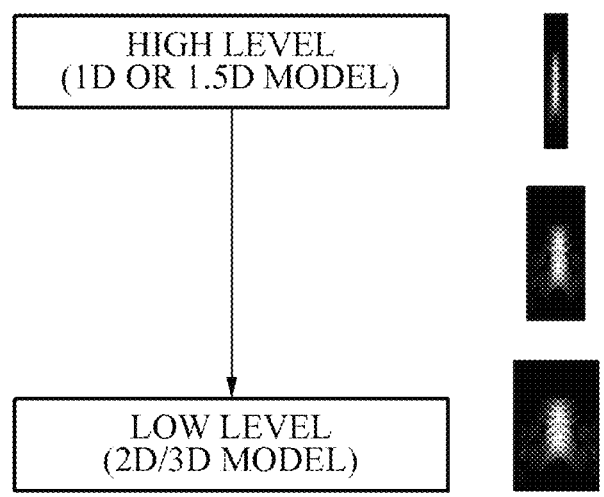
FIG. 3 is a diagram illustrating an example of a method of estimating a multiscale level point spread function (PSF).

FIG. 3 illustrates an example of a method of estimating a multiscale level point spread function (PSF). PSFs illustrated on a right side of FIG. 3 will be described by comparing PSFs at a high level, for example, a one-dimensional (1D) model or a one and a half-dimensional (1.5D) model including smaller widths in a lateral direction, with PSFs at a low level, for example, a 2D model or a 3D model.

As shown in FIG. 3, a ratio of a width in an axial direction to a width in a lateral direction is relatively greater for each of the PSFs at the high level, when compared to the PSFs at the low level. That is, a width in the lateral direction or in an elevation direction is relatively small for each of the PSFs at the high level, when compared to the PSFs at the low level. A PSF at each multiscale level is estimated from a deconvoluted image with a previously-estimated PSF at each level progressively expanding to the low level.

Figure 4:
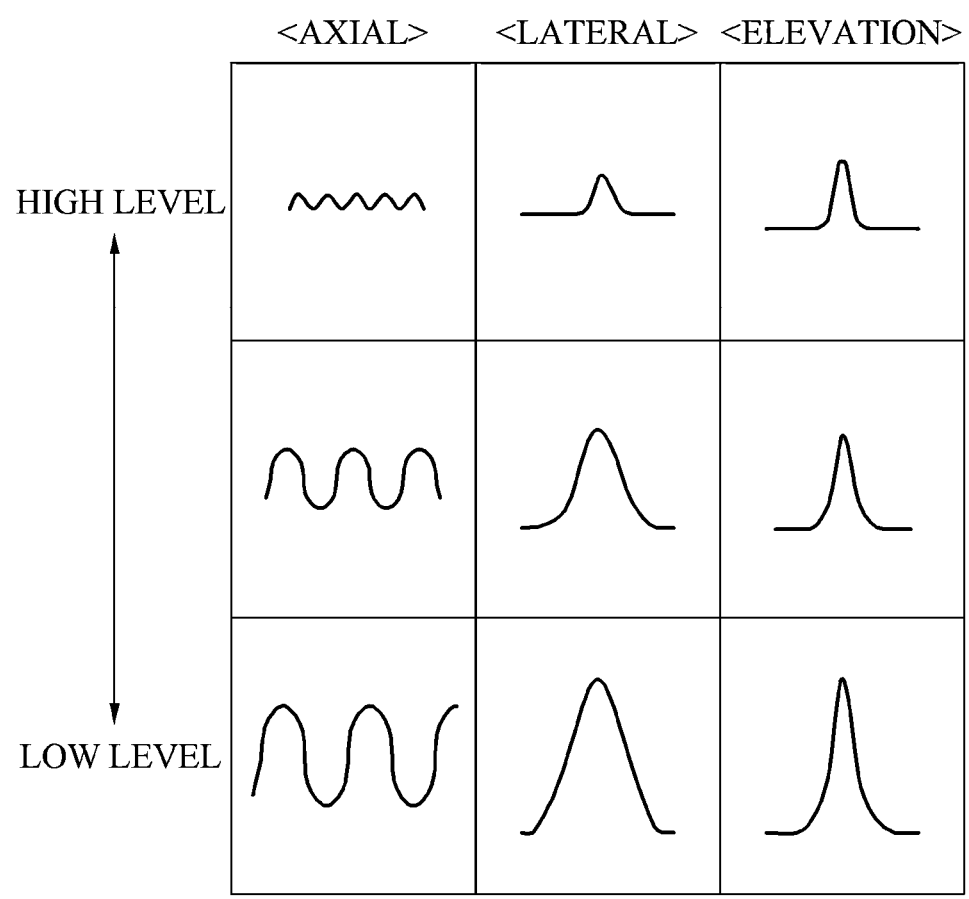
FIG. 4 is a diagram illustrating examples of bases used in a method of estimating a PSF.

FIG. 4 illustrates examples of bases used in a method of estimating a PSF. Comparing bases to be applied to an axial direction of the PSF, a basis to be applied to the axial direction that includes a relatively narrow width may be selected at a high level, and a basis to be applied to the axial direction that includes a relatively wide width may be selected at a low level.

Bases differing from the bases to be applied to the axial direction may be selected to be applied to a lateral direction and an elevation direction (i.e., a magnitude direction), respectively, of the PSF. The foregoing description can be understood by referring to a difference in a PSF at each multiscale level, as shown in FIG. 3.

For example, the PSF estimator 130 of FIG. 1 may select a basis at the high level, and may apply the selected basis to an original PSF to make a width of the original PSF narrower. That is, the PSF estimator 130 may select bases at each multiscale level progressively expanding toward the low (i.e., lowest) level based on the width of the original PSF to generate a more accurate PSF at each multiscale level. Based on this method, the PSF estimator 130 estimates a final PSF to update the original PSF. For example, a basis including a Gaussian basis may be selected to change a scale of a PSF, but may include a different scale change at each direction (e.g., axial and lateral).

Accordingly, a PSF may be estimated at each multiscale level by applying different bases to the axial direction, the lateral direction, and the elevation direction, respectively, of an original or previously-estimated PSF including a narrow width at the high level. Accordingly, a final PSF including a relatively wide width at the low level may be restored in a circular form while progressively expanding from the high level to the low level.

In the process of estimating the PSF at each multiscale level, a result of a PSF simulation may be used as an initial value of the original PSF when estimating the PSF at the high level. However, the initial value may not be limited thereto.

In another example, a value obtained by measuring a PSF in a real environment may be used as the initial value of the original PSF at the high level. The PSF in the real environment may be measured by inserting a wire or a ball made of a metallic material into an imaging phantom without a scatter reflection. In another example, the initial value of the original PSF at the high level may be designated based on a white noise. Accordingly, it should be understood that various modifications may be made to the designation of the initial value of the original PSF at the high level.

When the original PSF is estimated at the high level in the estimation of the PSF at each multiscale level, only a 1D PSF estimation in which only the axial direction is considered may be performed. A multi-dimensional PSF estimation in which other directions in addition to the axial direction are considered may be performed at lower levels.

Through the method described above, an accurate PSF may be estimated without an error in a phase, and the pattern h of the ultrasonic wave in Equation 1 may be estimated accurately. Accordingly, the scatter reflection f of the object may be estimated accurately, and an ultrasonic image including a high resolution may be generated. Although an example of a method of estimating a PSF of an ultrasonic image has been described, a method of progressively estimating and restoring a PSF at each multiscale level may be widely applicable to various fields including generation of an elastic image of a material, radar, sound signal processing, and/or other fields known to one of ordinary skill in the art.

Program instructions to perform a method described herein, or one or more operations thereof, may be recorded, stored, or fixed in one or more computer-readable storage media. The program instructions may be implemented by a computer. For example, the computer may cause a processor to execute the program instructions. The media may include, alone or in combination with the program instructions, data files, data structures, and the like. Examples of non-transitory computer-readable storage media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files including higher level code that may be executed by the computer using an interpreter. The program instructions, that is, software, may be distributed over network coupled computer systems so that the software is stored and executed in a distributed fashion. For example, the software and data may be stored by one or more computer readable storage mediums. Also, functional programs, codes, and code segments accomplishing the examples disclosed herein can be easily construed by programmers skilled in the art to which the examples pertain based on and using the flow diagrams and block diagrams of the figures and their corresponding descriptions as provided herein.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus configured to generate an ultrasonic image, the apparatus comprising:
    a transceiver configured to transmit an ultrasonic signal to an object, and receive an echo signal;
    a beam former configured to perform beamforming on the received echo signal to generate image data; and
    a point spread function (PSF) estimator configured to update a PSF of the ultrasonic signal at each multiscale level to update the image data, wherein a ratio of a width in an axial direction to a width in a lateral direction is relatively greater for the PSF at a high multiscale level compared to the PSF at a low multiscale level.

2. The apparatus of claim 1, further comprising:
    a renderer configured to generate the ultrasonic image comprising an increased resolution based on deconvolution of the updated PSF from the image data.

3. The apparatus of claim 1, wherein the PSF estimator is further configured to:
    apply different bases to the axial direction and the lateral direction of the PSF to update the PSF.

4. The apparatus of claim 1, wherein the PSF estimator is further configured to:
    select, at the high multiscale level, a basis to be applied to the axial direction of the PSF that comprises a relatively narrow width, to update the PSF; and
    select, at the low multiscale level, a basis to be applied to the axial direction of the PSF that comprises a relatively wide width, to update the PSF.

5. The apparatus of claim 1, wherein the PSF estimator is further configured to:
    estimate, at the high multiscale level, a one-dimensional PSF based on the axial direction of the PSF;
    estimate, at the low multiscale level, a multi-dimensional PSF based on the axial direction and other directions of the PSF; and
    update the PSF based on the one-dimensional PSF and the multi-dimensional PSF.

6. The apparatus of claim 1, wherein the PSF estimator is further configured to:
    set a value determined through a simulation as an initial value of the PSF.

7. The apparatus of claim 1, wherein the PSF estimator is further configured to:
    set a value measured in a real environment as an initial value of the PSF.

8. An apparatus configured to generate an ultrasonic image, the apparatus comprising:
    a transceiver configured to transmit an ultrasonic signal to an object, and receive an echo signal;
    a beam former configured to perform a delay-and-sum operation on the received echo signal to generate image data; and
    a point spread function (PSF) estimator configured to apply different bases to an axial direction and a lateral direction of a PSF of the ultrasonic signal to update the PSF and the image data.

9. The apparatus of claim 8, further comprising:
    a renderer configured to generate the ultrasonic image comprising a resolution corresponding to a required display environment based on deconvolution of the updated PSF from the image data.

10. The apparatus of claim 8, wherein the PSF estimator is further configured to:
    update the PSF at each multiscale level, wherein a ratio of a width in an axial direction to a width in a lateral direction is relatively greater for the PSF at a high multiscale level compared to the PSF at a low multiscale level.

11. The apparatus of claim 10, wherein the PSF estimator is further configured to:
    select, at the high multiscale level, a basis to be applied to the axial direction of the PSF that comprises a relatively narrow width, to update the PSF; and
    select, at the low multiscale level, a basis to be applied to the axial direction of the PSF that comprises a relatively wide width, to update the PSF.

12. A method of generating an ultrasonic image, the method comprising:
    transmitting an ultrasonic signal to an object;
    receiving an echo signal;

performing beamforming on the received echo signal to generate image data; and updating a point spread function (PSF) of the ultrasonic signal at each multiscale level to update the image data, wherein a ratio of a width in an axial direction to a width in a lateral direction is relatively greater for the PSF at a high multiscale level compared to the PSF at a low multiscale level.

13. The method of claim 12, further comprising:
generating the ultrasonic image comprising an increased resolution based on deconvolution of the updated PSF from the image data.

14. The method of claim 12, wherein the updating comprises:
applying different bases to the axial direction and the lateral direction of the PSF to update the PSF.

15. The method of claim 12, wherein the updating comprises:
selecting, at the high multiscale level, a basis to be applied to the axial direction of the PSF that comprises a relatively narrow width, to update the PSF; and
selecting, at the low multiscale level, a basis to be applied to the axial direction of the PSF that comprises a relatively wide width, to update the PSF.

16. A non-transitory computer-readable storage medium storing a program to generate an ultrasonic image, comprising instructions to cause a computer to perform the method of claim 12.

17. A method of generating an ultrasonic image, the method comprising:
transmitting an ultrasonic signal to an object;
receiving an echo signal;
performing a delay-and-sum operation on the received echo signal to generate image data; and
applying different bases to an axial direction and a lateral direction of a point spread function (PSF) of the ultrasonic signal to update the PSF and the image data.

18. The method of claim 17, wherein the applying comprises:
updating the PSF at each multiscale level, wherein a ratio of a width in an axial direction to a width in a lateral direction is relatively greater for the PSF at a high multiscale level compared to the PSF at a low multiscale level.

19. The method of claim 18, wherein the applying comprises:
selecting, at the high multiscale level, a basis to be applied to the axial direction of the PSF that comprises a relatively narrow width, to update the PSF; and
selecting, at the low multiscale level, a basis to be applied to the axial direction of the PSF that comprises a relatively wide width, to update the PSF.

20. A non-transitory computer-readable storage medium storing a program to generate an ultrasonic image, comprising instructions to cause a computer to perform the method of claim 17.

* * * * *